US008520302B2

(12) United States Patent
Graber (10) Patent No.: US 8,520,302 B2
(45) Date of Patent: Aug. 27, 2013

(54) STAND FOR A MICROSCOPE, IN PARTICULAR A SURGICAL MICROSCOPE

(75) Inventor: Michael Graber, Horn (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 386 days.

(21) Appl. No.: 13/039,434

(22) Filed: Mar. 3, 2011

(65) Prior Publication Data

US 2011/0216403 A1    Sep. 8, 2011

(30) Foreign Application Priority Data

Mar. 4, 2010    (DE) .......................... 10 2010 010 133

(51) Int. Cl.
*G02B 21/00* (2006.01)
*A47H 1/10* (2006.01)
(52) U.S. Cl.
USPC .......................................... 359/384; 248/324
(58) Field of Classification Search
USPC .......................................... 359/384; 248/324
See application file for complete search history.

(56) References Cited

U.S. PATENT DOCUMENTS

| 4,339,100 A | 7/1982 | Heller et al. |
| 4,815,832 A | 3/1989 | Nagano et al. |
| 6,199,812 B1 | 3/2001 | Schuepbach |
| 6,899,307 B2 | 5/2005 | Strauss et al. |
| 2002/0014562 A1* | 2/2002 | Twisselmann ........... 248/123.11 |
| 2003/0117703 A1 | 6/2003 | Metelski |

* cited by examiner

*Primary Examiner* — Alessandro Amari
(74) *Attorney, Agent, or Firm* — Hodgson Russ LLP (57) ABSTRACT

The present invention relates to a microscope stand (11), in particular a stand for a surgical microscope, including a pivot support (12) and a mount (22) for mounting the microscope (16) to the microscope stand (11). The mount (22) is supported about a first axis of rotation (23) so that it is rotatable relative to pivot support (12) and capable of being braked, the mount being connected via braking force transmission means (30) to a brake (26), which defines a second axis of rotation (27) extending parallel to first axis of rotation (23). The braking force transmission means (30) include two transfer levers (31; 36), whose two ends (32, 33; 37, 38) are connected without play to the mount (22) and the brake (26), respectively, by respective pivot points (41, 46, 51, 56), which are radially spaced apart from their respective axes of rotation (23, 27).

16 Claims, 5 Drawing Sheets

STAND FOR A MICROSCOPE, IN PARTICULAR A SURGICAL MICROSCOPE

CROSS REFERENCE TO RELATED APPLICATIONS

This application claims priority of German patent application number 10 2010 010 133.8 filed Mar. 4, 2010, the entire disclosure of which is incorporated by reference herein.

FIELD OF THE INVENTION

The present invention relates to a microscope stand, in particular to a stand for a surgical microscope, of the type comprising at least one pivot support and a mount for mounting the microscope to the microscope stand, the mount being supported about a first axis of rotation so that it is rotatable relative to the pivot support and capable of being braked and further being connected via braking force transmission means to a brake, which defines a second axis of rotation extending parallel to the first axis of rotation.

BACKGROUND OF THE INVENTION

Microscopes, particularly surgical microscopes, are supported by microscope stands and surgical microscope stands, respectively, which may be placed on a floor or a piece of furniture or equipment, or be mounted to a wall or ceiling. Such microscope stands include at least one pivot support and a mount for mounting the microscope to the microscope stand. In order to be able to rotate the microscope relative to the pivot support, and thus, to adapt its orientation to the requirements of the particular environment, it is known to support the mount in such a way that it is rotatable relative to the pivot support about a first axis of rotation. Moreover, in order to prevent the microscope from being accidentally moved out of alignment with respect to the pivot support, it is also known to connect the mount via braking force transmission means to a brake, which defines a second axis of rotation extending parallel to the first axis of rotation.

In a microscope stand marketed by the applicant, the mount is connected to the brake via a first gear wheel mounted centrally with respect to the second axis of rotation and a gear segment whose center of rotation is disposed centrally with respect to the first axis of rotation (oscillating gear segment drive), said gear wheel and said gear segment constituting the braking force transmission means. This approach is highly reliable and has proven successful on the market. It also optimizes the available space.

However, the drawback of the known approach is that the oscillating gear segment drive must have sufficient play to ensure proper operation. Moreover, an adjustment device must be provided for the gear wheels so as to allow adjustment of the play therebetween. This requires additional mechanical means, which typically are complex and increase manufacturing cost of a microscope stand.

Therefore, there is still a need to improve a microscope stand, and in particular a stand for a surgical microscope, in such a way that it does not have the aforementioned disadvantages and, in particular, that it provides a reliable and easy-to-manufacture connection between the mount and the brake without requiring increased height or additional devices.

SUMMARY OF THE INVENTION

This object is achieved by the features of the independent claims. Advantageous embodiments are illustrated in the figures and described in the dependent claims.

In accordance with the present invention, the braking force transmission means include at least one transfer lever, whose two ends are connected without play to the mount and the brake, respectively, by respective pivot points, which are radially spaced apart from their respective axes of rotation.

The play-free connection eliminates the need for a mechanism for positioning the two parallel, spaced apart axes of rotation relative to each other. In this context, the term "play-free" is understood to mean "substantially play-free", so that, if at all, only little play, and particularly preferably no play, is present at the respective pivot points.

Since the at least one transfer lever is connected directly, and because there is no need for an adjustment mechanism for adjusting play, an overall more compact design can be achieved for this portion of microscope stand as compared to the previously known approaches. Double row, preloaded angular contact ball bearings have proven to be ideal.

The brake and the mount do not necessarily have to be mounted on the free end of the respective pivot support.

Advantageously, the mount is provided by a connection unit, such as a connection plate, to which the microscope may be directly attached. In this context, the term "mount" is understood to include also a multi-part design, which may have interconnected arm members, as long as the microscope can be fixedly attached to this mount.

With the approach of the present invention, no noise is generated when the mount is rotated relative to the pivot support, as would occur in the case of a oscillating gear segment drive, for example. Moreover, this kind of braking force transmission means makes it possible to achieve larger pivoting ranges of the mount relative to the pivot support without requiring more space, as would be the case in a known oscillating gear segment drive.

Preferably, the radial distance of the second pivot point from the first axis of rotation differs from that of the first pivot point from the second axis of rotation, thereby permitting a rotational speed conversion from the brake to the mount, respectively from the mount to the brake. This makes it possible, for example, to optimize the size of the brake and the braking force generated by the brake, and may allow the brake to be made smaller than would be possible in the case of direct force transmission.

Preferably, the two pivot points of the transfer lever define respective pivot axes provided in a plane extending parallel to the plane containing the axes of rotation of the mount and the brake. This ensures that transmission of the rotary motion is possible in any position of the pivot points relative to each other, and that the system will not assume a dead center position.

Preferably, the transfer lever is curved between the pivot points, preferably outwardly with respect to one of the axes of rotation, which allows for optimal space utilization and also avoids a dead center position of the system.

Preferably, at least one of the pivot points is provided by a pivot pin and an opening surrounding the pivot pin. This permits a simple design for the pivot point. Preferably, a radial bearing is received between the opening and the pivot pin. The pivot pin includes, for example, a cam, a pin, or a screw whose shank ensures a bolt-like action of the screw. Advantageously, the edge of the opening completely surrounds the pivot pin, allowing high forces to be transmitted by the pivot point. Alternatively, the opening surrounds the pivot pin over at least half of its circumference. This may simplify the assembly of the pivot point. At its distal end, the pivot pin has a formation for engagement of a tool, while at its proximal end, it is screwed into the carrier body of the rotation axis member.

Preferably, the pivot pin projects beyond a plane defined by the mount, and the opening surrounding the pivot pin is provided on the corresponding end of the transfer lever. The pivot pin may be formed or disposed directly on the mount and/or on the brake, for example on the housing thereof. Alternatively, an additional, preferably disk-shaped carrier body or carrier element is provided, on which the corresponding pivot pin is formed or disposed.

Preferably, a disk-shaped supporting element is provided which is disposed parallel to the plane defined by the mount and which has a recess for receiving the corresponding end of the transfer lever. This supporting element is advantageously arranged centrally with respect to the first axis of rotation, and in all positions of the mount relative to the pivot support, said supporting element prevents the corresponding end of the transfer lever from being displaced sideways. For example, the supporting element has a U-shape in a cross section transverse to the pivot plane of the transfer lever, and the bottom portion connecting the sides provides stop means for limiting the maximum pivoting range of the mount. Alternatively, the supporting element may be completely spaced apart from the plane defined by the mount, so that the mount is pivotable through 360°. In accordance with the present invention, such an alternative approach is possible, but not preferred because it lacks a natural end stop, and thus, a natural limiting pivot position. The corresponding end of the transfer lever is advantageously articulated between the supporting element and the plane defined by the mount.

Preferably, at least two transfer levers are provided as braking force transmission means, which results in increased stability of the connection between the mount and the brake.

Preferably, the two pivot points of a transfer lever define respective pivot axes that are in each case provided in one plane, the two planes (one plane for each of the two transfer levers) extending parallel to, and on both sides of, the plane containing the axes of rotation. The two transfer levers are parallel support links, which enable the rotary motion to be transmitted from the mount to the brake in a simple and stable manner.

Preferably, the pivot points of the two transfer levers are disposed diametrically opposite one another with respect to the first axis of rotation and/or the second axis of rotation, which allows the connection to be configured symmetrically at least with respect to one of the axes of rotation. It is particularly preferred for the connection to be symmetrical with respect to both axes of rotation so as to prevent stresses from occurring within the connection as a result of asymmetrical force transmission. A symmetrical configuration of the connection renders it highly suitable for use in practice and enables easy manufacture of the connection, and thus of the microscope stand.

Preferably, the transfer levers lie in two different planes, which advantageously extend parallel to each other, as a result of which the mount would be pivotable through 360°. Advantageously, a disk-shaped carrier body is in each case provided between the transfer levers centrally with respect to the axes of rotation to serve as a carrier element on which may be formed or disposed the pivot pins of the pivot points.

In an alternative embodiment of the present invention, the transfer levers lie in a common pivot plane, which allows for a compact design of the connection. The maximum pivoting range of the mount is advantageously limited by the mutual engagement of the transfer levers against each other (rotational end stop).

Preferably, at least one of the transfer levers has a recess formed on the side facing the other transfer lever and adapted to partially receive a portion of the other transfer lever so as to increase the pivoting range of the mount. Advantageously, both transfer levers have such recesses on their mutually facing sides. Transfer levers of this kind can be symmetrical with respect to one another and are therefore economic to manufacture.

Preferably, a parallel guide mechanism in the form of a cross-lever linkage is provided which is designed according to one of the claims of commonly owned German patent application number 10 2010 010 131.1 filed Mar. 4, 2010, which makes it possible to make a microscope stand, in particular a stand for a surgical microscope, that, in addition to the aforementioned advantages, also has the advantages of said cross-lever linkage. The aforementioned German patent application number 10 2010 010 131.1 is incorporated herein by reference in its entirety in order to allow a later combination of the two applications based on the same priority.

Similarly, the pivot support is preferably designed according to one of the claims of international patent application WO 98/52484 A1, which makes it possible to make a microscope stand, in particular a stand for a surgical microscope, that, in addition to the aforementioned advantages, also has the advantages of this known pivot support. U.S. Pat. No. 6,199,812 corresponding to international patent application WO 98/52484 A1 is incorporated herein by reference in its entirety in order to allow a later combination of the two or three applications based on the same priority. For a description of the pivot support, reference is explicitly made to the figures and their description in the cited U.S. Pat. No. 6,199,812 and corresponding international application WO 98/52484 A1.

The list of reference numerals is part of the disclosure.

BRIEF DESCRIPTION OF THE DRAWING VIEWS

The present invention is schematically described in more detail by way of example and with reference to figures.

The figures are described collectively. Identical reference numerals denote identical components; reference numerals having different indices indicate functionally identical or similar components.

In the drawing.

DETAILED DESCRIPTION OF THE INVENTION

Microscope stand 11 illustrated in FIGS. 1 through 4 is a stand for a surgical microscope, including a C-shaped pivot support 12 which is connected at a first end 13 to a stand interface 14 and is pivotable relative thereto.

Figure 1:
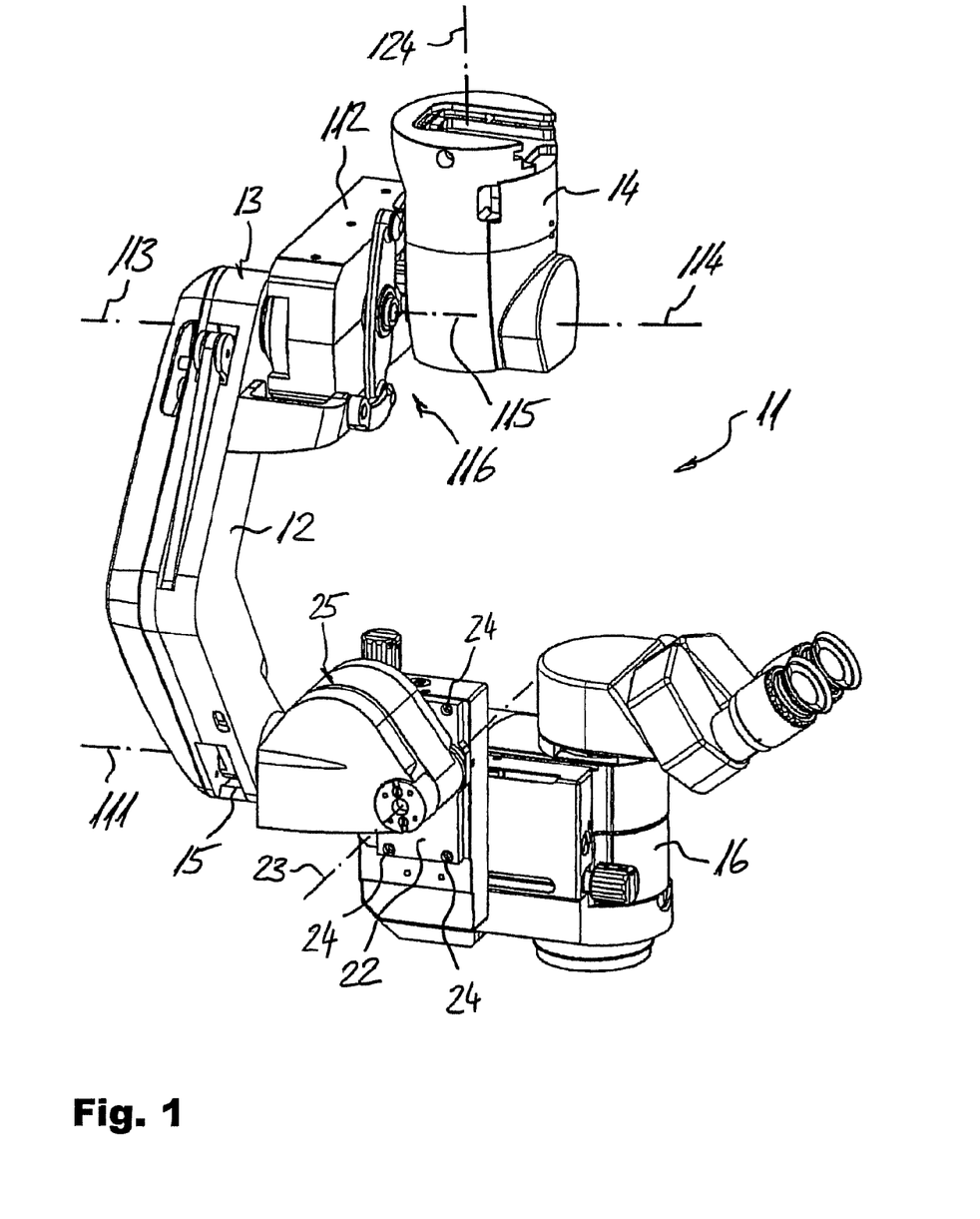
FIG. 1 is a perspective view of a microscope stand, shown with a mount in a first position.
Figure 2:
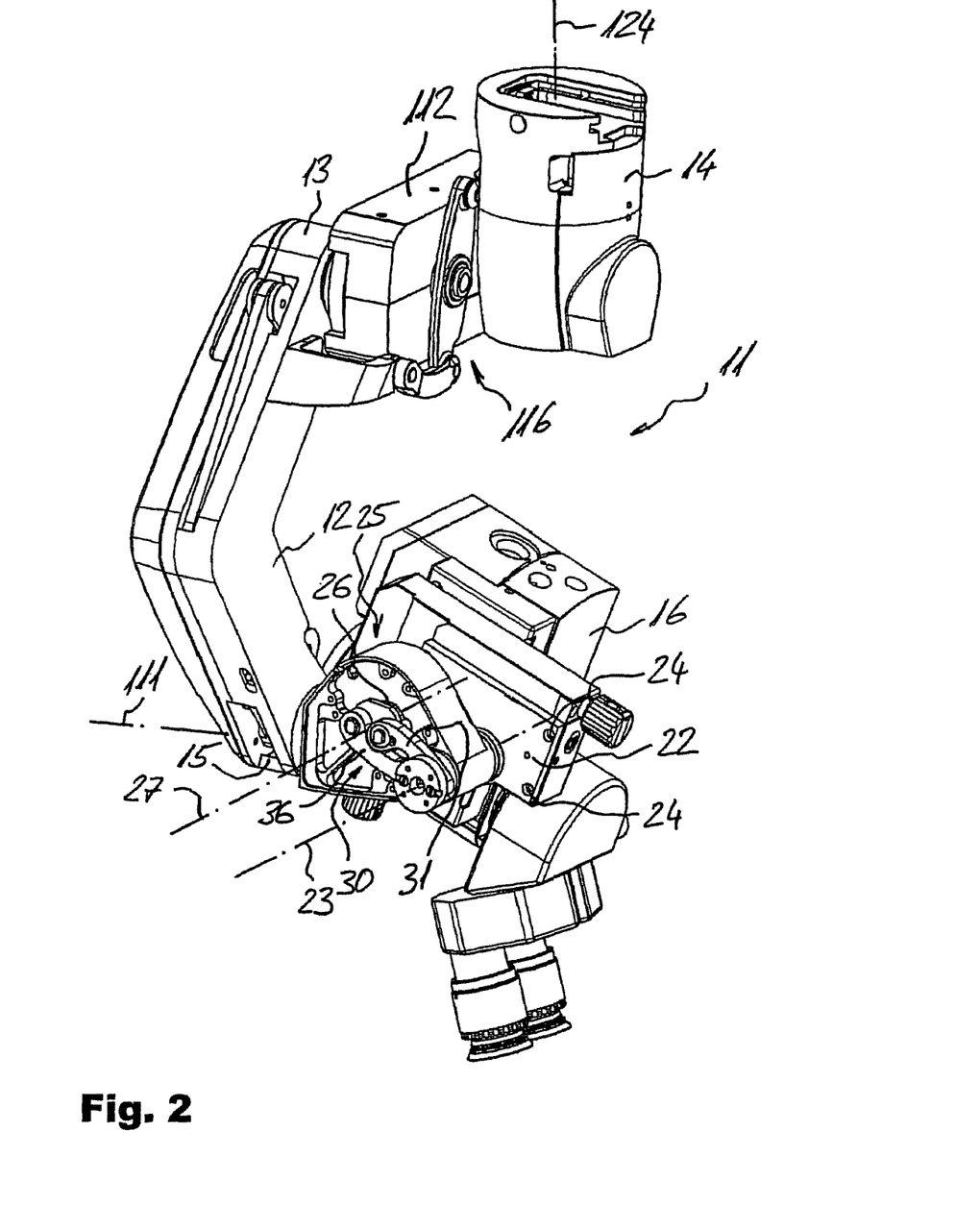
FIG. 2 is a view of the microscope stand of FIG. 1, shown with the mount in a second position.

Stand interface 14 serves for attachment to at least one further support arm of microscope stand 11, for example, to a ceiling mount, a floor stand, or to a wall mount. In this example, stand interface 14 is mounted to a ceiling bracket (not shown here), which allows attachment of microscope stand 11 to a ceiling. Stand interface 14 is rotatable about a rotation axis 124 relative to the ceiling bracket.

The design of pivot support 12 is analogous to that of the pivot support according to one of the claims and figures of the applicant's international patent application WO 98/52484 A1 corresponding to U.S. Pat. No. 6,199,812. Pivot support 12 is pivotable about a support axis/axle 113 held by C-slide displacement assembly 112. C-slide displacement assembly 112 is pivotable about a pivot axis 114 relative to stand interface 14. All pivoting movements can be suppressed by braking force. Pivot support 12 is held to stand interface 14 by a parallel guide mechanism 116, which allows pivot support 12 to perform a circular motion in a vertical plane. Parallel guide mechanism 116 is formed by a cross-lever linkage which is rotatable about a cross-lever axis 115 extending centrally between and parallel to support axis 113 of pivot support 12 and pivot axis 114 of C-slide displacement assembly 112.

Parallel guide mechanism 116, respectively the cross-lever linkage, is designed according to one of the claims and figures of German patent application no. 10 2010 010 131.1 filed on the same day (Mar. 4, 2010) as German patent application no. 10 2010 010 133.8 from which the present application claims priority.

The other, second end 15 of pivot support 12 is provided with a mount 22 for mounting microscope 16 to microscope stand 11. Mount 22 is connected to pivot support 12 via a braking device 25 fixedly mounted on the pivot support. The braking device is pivotable about mount axis 111. Mount 22 includes a connection plate having holes 24 through which fastening elements can be passed for attachment of microscope 16 thereto.

Mount 22 is supported about a first axis of rotation 23 so that it is rotatable relative to pivot support 12 and capable of being braked, the mount being connected via braking force transmission means 30 to a brake 26, which defines a second axis of rotation 27 extending parallel to first axis of rotation 23. Braking force transmission means 30 include two transfer levers 31, 36, whose two ends 32 and 33, respectively 37 and 38, are connected without play to mount 22 and brake 26, respectively, by respective pivot points 41 and 46, respectively 51 and 56, which are radially spaced apart from their respective axes of rotation 23 and 27. Transfer levers 31 and 36 lie in a common pivot plane. Pivot points 41 and 51, respectively 46 and 56, of the two transfer levers 31 and 36 are in each case disposed diametrically opposite one another with respect to first axis of rotation 23 and second axis of rotation 27. In addition, the two pivot points 41 and 46, respectively 51 and 56, of a transfer lever 31, respectively 36, define associated pivot axes (extending normal to the page in FIGS. 3 and 4) that are for each transfer lever provided in one plane. These two planes (one for transfer lever 31, another for transfer lever 36) extend parallel to, and on both sides of, the plane containing the axes of rotation 23 and 27.

Figure 3:
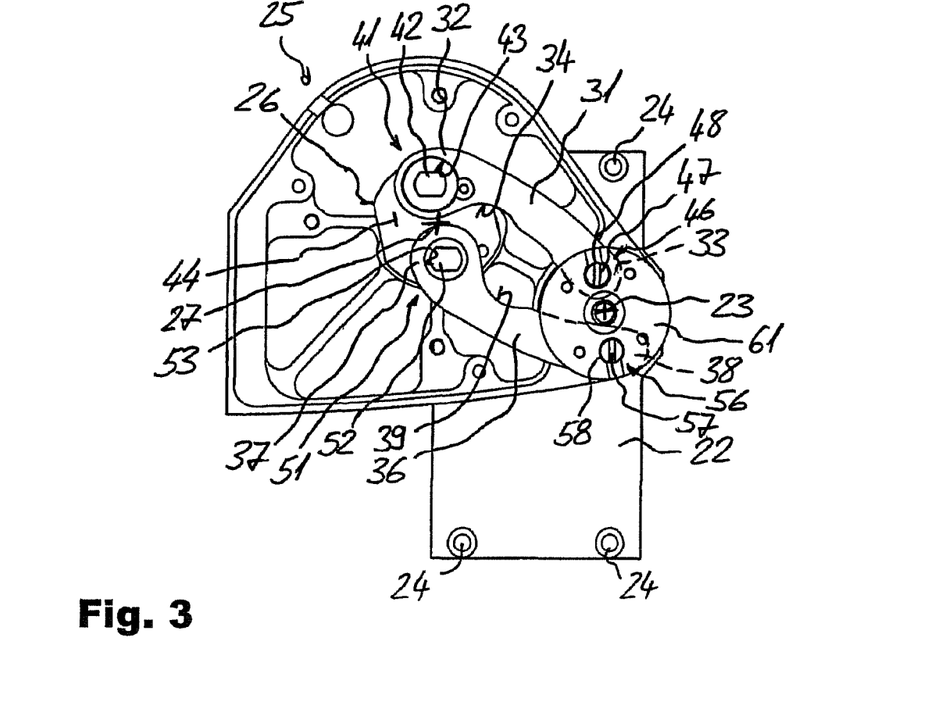
FIG. 3 is a detail view of the braking force transmission means, shown with the mount in a first position.
Figure 4:
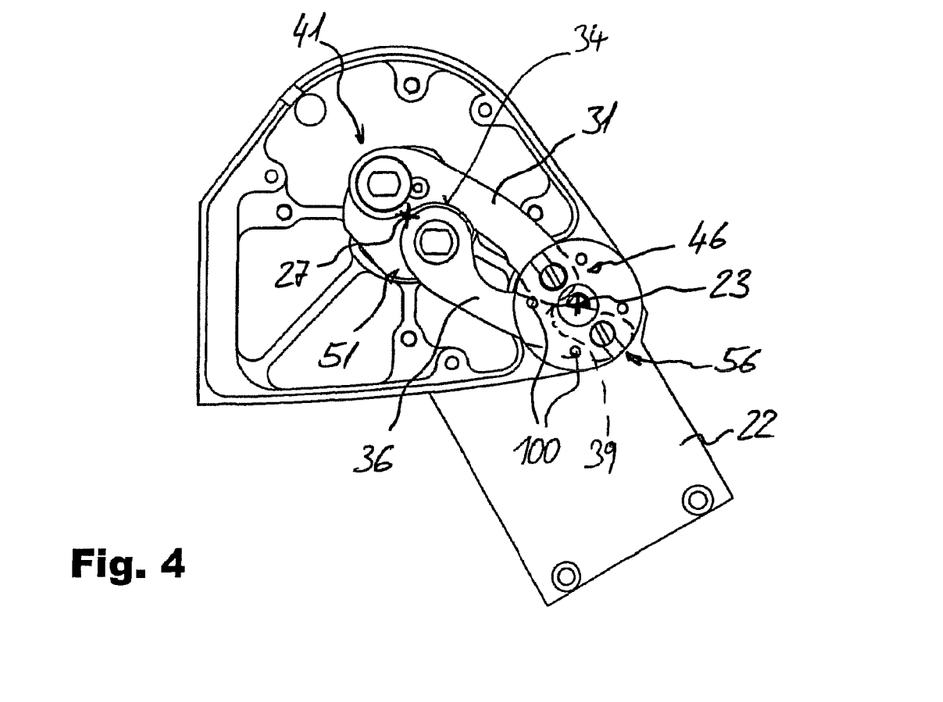
FIG. 4 is a detail view similar to FIG. 3, showing the mount in a position different from the first position.

Transfer levers 31 and 36 are curved outwardly between pivot points 41 and 46, respectively 51 and 56. Transfer levers 31 and 36 each have a recess 34, respectively 39, formed on the side facing the other transfer lever 36, respectively 31, and adapted to partially receive a portion of the other transfer lever 36, respectively 31.

Pivot points 41 and 51 have the same radial distance from second axis of rotation 27. Similarly, pivot points 46 and 56 have the same radial distance from first axis of rotation 23, the radial distances of pivot points 41 and 51 as well as pivot points 46 and 56 at the two axes of rotation 23 and 27 in each case being identical. Pivot points 41, 46, 51 and 56 are each provided by a pivot pin 42, 47, 52 or 57 and an opening 43, 48, 53 or 58 provided in transfer lever 31, respectively 36, and surrounding the respective pivot pin 42, 47, 52 or 57. Pivot pins 41 and 52 are provided on a disk-shaped first carrier body 44 such that they project therefrom and beyond a plane defined by mount 22, said carrier body providing second axis of rotation 27. Pivot pins 47 and 57 are provided on a disk-shaped supporting element 61 and project beyond a plane defined by mount 22. Pivot pins 47 and 57 are formed by screws which are passed through supporting element 61.

Openings 43 and 48, respectively 53 and 58, which are provided on the respective ends 32, 33 and 37, 38 of first and second transfer levers 31 and 36 and which surround pivot pins 42 and 47, respectively 52 and 57, are each configured as peripherally enclosed openings. Insert elements in the form of, for example, preloaded angular contact ball bearings 101, may be provided between openings 43 and 48, respectively 53 and 58, and the corresponding pivot pins 42 and 47, respectively 52 and 57, to improve the sliding properties of pivot points 41, 46, 51 and 56.

Disk-shaped supporting element 61 is disposed parallel to the plane defined by mount 22 and has a U-shape in a cross section transverse to the pivot plane of transfer levers 31 and 36. The spaced-apart sides of supporting element 61, which is arranged centrally with respect to first axis of rotation 23, form a recess 33 for receiving first transfer lever 31 and for receiving end 38 of second transfer lever 36. Supporting element 61 serves to support transfer levers 31 and 36 on both sides. Moreover, as indicated, four mounting holes 100 may be provided as an additional interface, for attachment of, for example, a handle.

When in the pivoted positions shown in FIG. 4, transfer levers 31 and 36 rest against each other, so that second transfer lever 36 engages in first recess 34 and mount 22 is unable to pivot further (rotational end stop, comparable to the engagement of first transfer lever 31 in second recess 39).

Figure 5:
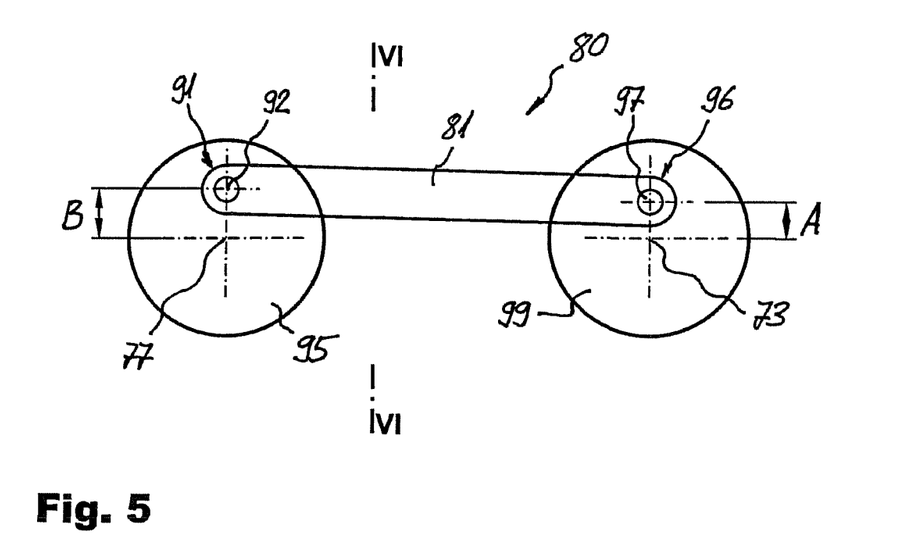
FIG. 5 is a schematic view of a second exemplary embodiment of the braking force transmission means.
Figure 6:
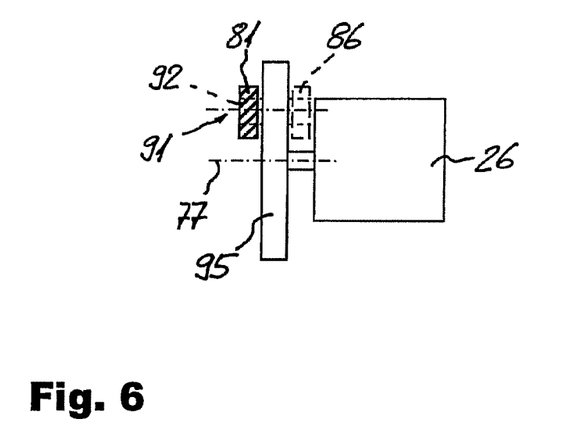
FIG. 6 is a cross-sectional view of the braking force transmission means shown in FIG. 5, taken along line VI-VI of FIG. 5.

FIGS. 5 and 6 schematically show a braking force transmission means 80 which differs from braking force transmission means 30 described above in the configuration and arrangement of first transfer lever 81. Pivot pins 92 and 97 are provided on equally oriented sides of respective disk-shaped carrier bodies 95 and 99.

Second pivot point 96 is spaced from first axis of rotation 73 by a radial distance A. First pivot point 91 is spaced from second axis of rotation 77 by a radial distance B, which is different, here greater, than radial distance A of second pivot point 96. In this manner, speed conversion is provided.

In order to increase, for example, the structural rigidity of braking force transmission means 80, a second transfer lever 86 (shown in dashed lines in FIG. 6) may be provided, said second transfer lever being disposed behind first transfer lever 81 with respect to the view of FIG. 5. Transfer levers 81 and 86 lie in two different pivot planes extending parallel to each other.

Although only this particular arrangement is illustrated here, it will be apparent to those skilled in the art that the radial distance is chosen according to the desired speed conversion ratio. From the foregoing description, those skilled in the art will further appreciate that radial distance A may also be selected to be greater than radial distance B, as the case may be.

Figure 7:
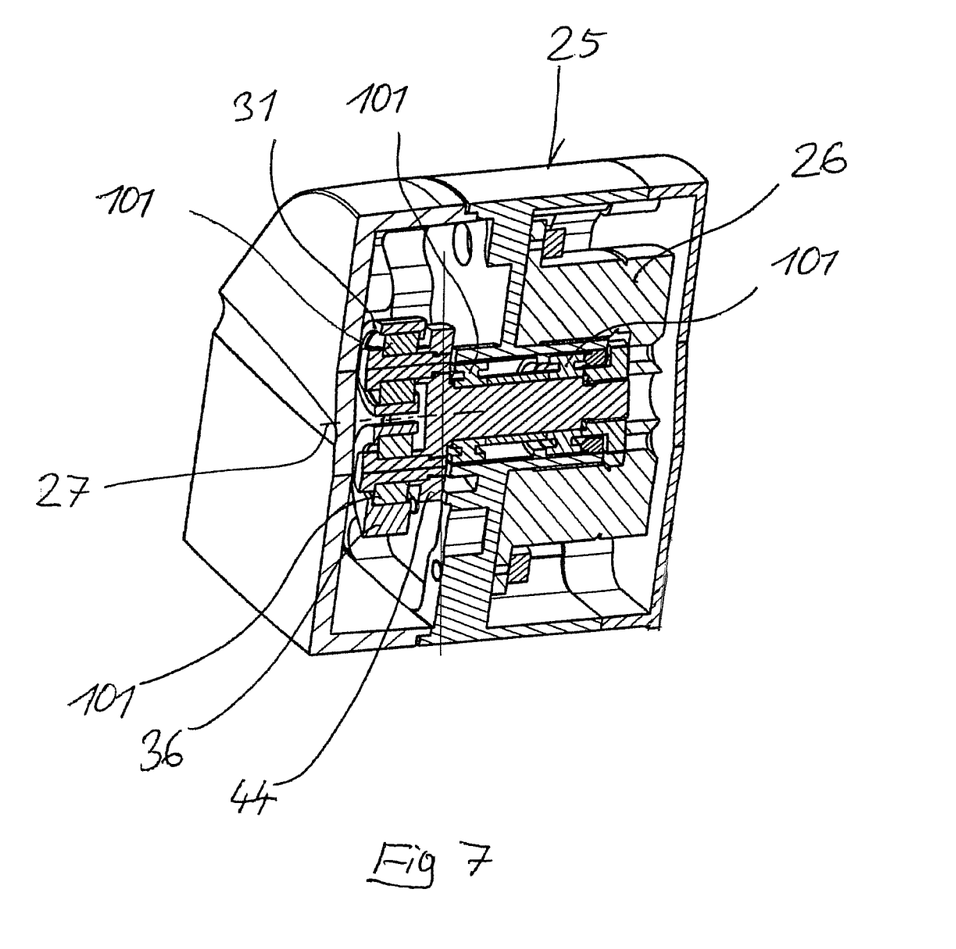
FIG. 7 is a cross section through the first rotation axis member.

FIG. 7 shows the design of first carrier body 44, which provides second axis of rotation 27. Also shown are double row angular contact ball bearings 101, which are preloaded and, therefore, allow rotation without radial play, and thus, transmission of braking force.

LIST OF REFERENCE NUMERALS 11 microscope stand
12 pivot support
13 $1^{st}$ end of 12
14 stand interface
15 $2^{nd}$ end of 12
16 microscope
22 mount
23 $1^{st}$ axis of rotation
24 hole in 22
25 braking device
26 brake
27 $2^{nd}$ axis of rotation
30 braking force transmission means
31 $1^{st}$ transfer lever
32 $1^{st}$ end of 31
33 $2^{nd}$ end of 31
34 $1^{st}$ recess
36 $2^{nd}$ transfer lever
37 $1^{st}$ end of 36
38 $2^{nd}$ end of 36
39 $2^{nd}$ recess
41 $1^{st}$ pivot point
42 $1^{st}$ pivot pin
43 $3^{rd}$ opening
44 $1^{st}$ carrier body at 27
46 $2^{nd}$ pivot point
47 $2^{nd}$ pivot pin
48 $4^{th}$ opening
51 $3^{rd}$ pivot point
52 $3^{rd}$ pivot pin
53 $5^{th}$ opening
56 $4^{th}$ pivot point
57 $4^{th}$ pivot pin
58 $6^{th}$ opening
61 supporting element
73 $1^{st}$ axis of rotation
77 $2^{nd}$ axis of rotation
80 braking force transmission means
81 $1^{st}$ transfer lever of 80
86 $2^{nd}$ transfer lever of 80
91 $1^{st}$ pivot point of 80
92 $1^{st}$ pivot pin of 80
95 $1^{st}$ carrier body of 80
96 $2^{nd}$ pivot point of 80
97 $3^{rd}$ pivot pin of 80
99 2nd carrier body of 80
100 mounting hole
101 angular contact ball bearing
111 mount axis
112 C-slide displacement assembly
113 support axis
114 pivot axis
115 cross-lever axis
116 parallel guide mechanism
124 rotation axis of 14

What is claimed is:

1. A microscope stand for supporting a surgical microscope, the stand comprising:
at least one pivot support;
a mount for mounting the surgical microscope to the microscope stand, the mount being supported about a first axis of rotation to be rotatable relative to the pivot support;
a brake which defines a second axis of rotation extending parallel to the first axis of rotation;
a braking force transmission means connecting the brake to the mount for enabling the mount to be braked, wherein the braking force transmission means includes at least one transfer lever having a first end connected without play to the brake by at least one first end pivot point and a second end connected without play to the mount by at least one second end pivot point and wherein the second end pivot point is radially spaced apart from the first axis of rotation by a first radial distance and the first end pivot point is radially spaced apart from the second axis of rotation by a second radial distance (B).

2. The microscope stand as recited in claim 1, wherein the first radial distance differs from the second radial distance.

3. The microscope stand as recited in claim 1, wherein the first end pivot point and the second end pivot point of the transfer lever define respective pivot axes that lie in a plane extending parallel to a plane containing the first and second axes of rotation.

4. The microscope stand as recited in claim 1, wherein the transfer lever is curved between the first end pivot point and the second end pivot point.

5. The microscope stand as recited in claim 4, wherein the transfer lever is curved outwardly with respect to at least one of the first and second axes of rotation.

6. The microscope stand as recited in claim 1, wherein at least one of the pivot points is provided by a pivot pin and an opening in the transfer lever surrounding the pivot pin.

7. The microscope stand as recited in claim 6, wherein the pivot pin projects beyond a plane defined by the mount, and the opening surrounding the pivot pin is provided on the corresponding end of the transfer lever.

8. The microscope stand as recited in claim 1, further comprising a disk-shaped supporting element disposed parallel to a plane defined by the mount, wherein the disk-shaped supporting element has a recess for receiving the second end of the transfer lever.

9. The microscope stand as recited in claim 1, wherein the braking force transmission means includes at least two transfer levers configured to engage one another to provide a rotational end stop.

10. The microscope stand as recited in claim 9, wherein the first end and second end pivot points of one of the two transfer levers define respective pivot axes that lie in a first plane parallel to a plane containing the first and second axes of rotation, and the first end and second end pivot points of the other of the two transfer levers define respective pivot axes that lie in a second plane parallel to the plane containing the first and second axes of rotation, wherein the first and second planes are on opposite sides of the plane containing the first and second axes of rotation.

11. The microscope stand as recited in claim 10, wherein the first end pivot points of the two transfer levers are diametrically opposite one another with respect to the second axis of rotation.

12. The microscope stand as recited in claim 10, wherein the second end pivot points of the two transfer levers are diametrically opposite one another with respect to the first axis of rotation.

13. The microscope stand as recited in claim 9, wherein the two transfer levers lie in two different pivot planes extending parallel to each other.

14. The microscope stand as recited in claim 9, wherein the two transfer levers lie in a common pivot plane.

15. The microscope stand as recited in claim 14, wherein at least one of the two transfer levers has a recess formed on a side facing the other transfer lever and adapted to partially receive a portion of the other transfer lever.

16. The microscope stand as recited in claim 9, wherein the pivot points are defined by respective pivot pins and preloaded angular contact ball bearings around the pivot pins.

* * * * *